United States Patent [19]

Yamamori et al.

[11] 4,396,625

[45] Aug. 2, 1983

[54] TREATMENT OF GLAUCOMA OR OCULAR HYPERTENSION AND OPHTHALMIC COMPOSITION

[75] Inventors: Kaoru Yamamori, Kawanishi; Yoshihiro Komuro, Nishinomiya; Yoshiya Yamahira, Ibaraki; Takeshi Noguchi, Takatsuki, all of Japan

[73] Assignee: Sumitomo Chemical Company, Limited, Japan

[21] Appl. No.: 257,563

[22] Filed: Apr. 27, 1981

[30] Foreign Application Priority Data

May 13, 1980 [JP] Japan ................................. 55/63555
May 13, 1980 [JP] Japan ................................. 55/63556

[51] Int. Cl.³ ............................................. A61K 31/425
[52] U.S. Cl. ........................................................ 424/270
[58] Field of Search ........................................... 424/270

[56] References Cited

U.S. PATENT DOCUMENTS 3,932,400   1/1976   Hibino et al. ...................... 424/270

OTHER PUBLICATIONS

Brit. J. Ophthal., (1975), 59, 296–300, Elliott et al.
Brit. J. Ophthal., (1975), 59, 301–303, Bonomi et al.

*Primary Examiner*—Douglas W. Robinson
*Attorney, Agent, or Firm*—Wenderoth, Lind & Ponack

[57] ABSTRACT

Method for the treatment of glaucoma or ocular hypertension by topically applying to the eye an effective amount of 2-(3-tert.-butylamino-2-hydroxypropylthio)-4-(5-carbamoyl-2-thienyl)-thiazole or its acid addition salt to lower the intraocular pressure of the diseased eye.

17 Claims, No Drawings

TREATMENT OF GLAUCOMA OR OCULAR HYPERTENSION AND OPHTHALMIC COMPOSITION

The present invention relates to a treatment of glaucoma or ocular hypertension by ophthalmically applying an effective amount to lower the intraocular pressure of the eye of 2-(3-tert.-butylamino-2-hydroxypropylthio)-4-(5-carbamoyl-2-thienyl)-thiazole of the formula (I) or acid addition salt thereof.

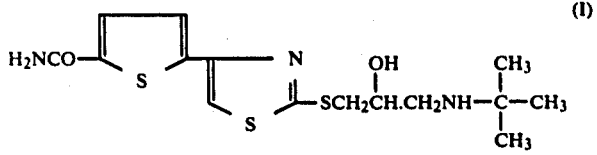

Glaucoma is an oculopathy caused by an excessive increase in an intraocular pressure, i.e. ocular hypertension, and a long duration of such hypertension, and finally causing a functional and structural impediment of eyes. For the treatment of glaucoma or ocular hypertension, various medicines like pilocarpine, epinephrine and the like have been used to lower the intra-ocular pressure, but many difficulties have been encountered in the actual clinical use thereof. That is, in the case of pilocarpine, there are many side-effects, after the ophthalmic application thereof, as stimulative pain, angiectasis, miosis and accompanying dark feeling, accommodative near-sight and the like. Furthermore, since the effective duration of lowering of intra-ocular pressure is comparatively short, it is necessary, in obtaining a longer working activity per application, to use a comparatively higher concentration of medicine, which is, as a matter of course, very dangerous to the patient. In the case of epinephrine, there are not only local efects such as ophthalmalgia and flow of tears after ophthalmic application, severe reactive conjunctival hyperemia at the time of effect-losing period and pigmentation in keratoconjuctiva in lengthy, repetitive use, but also systemic effects affecting the cardiac and circulation system.

The inventors, having studied hard to find an effective ophthalmic composition being free of the above-mentioned problems for the treatment of glaucoma or ocular hypertension, have found that the compound having the formula (I) and its acid addition salts do possess a strong intra-ocular pressure lowering effect, a long lasting effect, and no local and general side-effects after ophthalmic administration, and that they are very effective for the treatment of glaucoma in clinical use.

The ophthalmic composition of the present invention contains, as the main ingredient, the compound of the formula (I) or its acid addition salt. As the acid, use is made of an inorganic acid such as boric acid, hydrochloric acid, sulfuric acid, nitric acid and phosphoric acid, or an organic acid as acetic acid, oxalic acid, lactic acid, maleic acid, succinic acid, tartaric acid, fumaric acid, citric acid, glutaric acid, L-glutamic acid, d-camphor sulfonic acid, gluconic acid and the like. In preparing the present ophthalmic composition, an aqueous solution or suspension of 0.01 to 5%, preferably 0.1 to 1%, compound (I) or its salt is added with appropriate amounts of buffer, isotonic agent, preservative agent, bactericide, perfuming agents or the like. In case of an aqueous solution, an ophthalmic composition with the least irritative properties can be prepared by using D-mannitol as an isotonic agent and a combination of glycine and hydrochloric acid as buffer, thereby giving no formation of crystals in the solution of the active compound.

The intra-ocular pressure lowering effect of the present composition may be revealed at the eye administration dose of more than 0.00001 mg/kg body weight of the compound (I). Usually, the eye administration dose is 0.00001 to 1 mg/kg body weight, preferably 0.001 to 0.1 mg/kg, per application and 1 to 2 times application per day will be enough to give an effective lowering of intra-ocular pressure of the eye.

Toxicological studies of the compound (I) revealed that mouse acute toxicity expressed by $LD_{50}$ was more than 5000 mg/kg by oral administration and 500 mg/kg by intraperitoneal administration, and rat acute toxicity expressed by $LD_{50}$ was more than 3000 mg/kg by oral administration and 340 mg/kg by intraperitoneal administration. Even in toxic signs, no animals showed particular troublesome symptoms, and thus, the toxicity was indeed of a very lower order.

The present compound (I) can be prepared by the methods described in Japanese Patent Publication (examined) No. 39827/77 and No. 5670/78.

An ophthalmic aqueous solution of the present invention may be formulated, usually by using an acid addition salt of the compound (I) because of its higher solubility and excellent of intra-ocular pressure lowering activity, into 0.01 to 0.5 w/v %, preferably 0.1 to 0.5 w/v %, strength. In this case, the inventors have found that a less irritative ophthalmic composition substantially free from precipitation can be obtained by using D-mannitol as an isotonic agent and the combination of glycine and hydrochloric acid as buffer. In general, as an isotonic agent for ophthalmic composition, use has long been made of such members as sodium chloride, sodium nitrate, potassium nitrate and the like. Among them, sodium chloride is most widely accepted in the related field. Therefore, the inventors have first tried using this material for the isotonization of 0.01 to 0.5 w/v % aqueous solution of acid addition salt of compound (I). However, it was found that this material brought about the decrease in solubility of the acid addition salt and the precipitation of crystals out of the solution. The tendency was likewise found out with regard to potassium chloride, magnesium chloride, calcium chloride and lithium chloride. When the active ingredient is hardly soluble, it is, of course, possible to formulate a suspension in place of a solution. However, such a suspension will cause, with the lapse of time, agglomeration of particles and adhesion to the vessel, and will have an irritant action on the patient, accordingly. Therefore, for repeated applications for a longer period of time as required in the treatment of glaucoma, much preference is given to a solution form.

Next, the inventors have evaluated sodium nitrate and potassium nitrate as an isotonic agent for ophthalmic composition. In these cases, no crystalline deposit of acid addition salt of compound (I) was found, but the solution was colored yellowish brown. It was, thus, ascertained that the employment of such compound containing nitrate ion was improper under the circumstances. The inventors have finally found that D-mannitol is an ideal isotonic agent giving no formation of crystals and no coloration of the ophthalmic solution. Next, various buffers were examined. As a buffer for ophthalmic composition, there are boric, phosphoric, citric and acetic buffer systems. However, boric buffer will cause an excessive lowering of pH of the solution, possibly by the interaction with D-mannitol present, and citric buffer, as well as phosphoric and acetic buffers, will give an irritation to the eyes, accompanying with hot feeling, when administered.

As already stated, in the case that requires repeated applications of the ophthalmic composition for a longer period of time as in glaucoma, no irritation to eyes is a very important factor. As the result of our extensive studies, we have found that the particular combination of glycine and hydrochloric acid causes no irritant action to eyes. The effects of this combination of chemicals shall be more fully stated hereinunder (see Tables 1 and 2). In the present aqueous ophthalmic composition, if the concentration of active compound is less than 0.01 w/v %, the lowering of intra-ocular pressure is very weak, and if the concentration is more than 0.5 w/v %, the acid addition salt of compound (I) is hardly soluble, and is thereby unable to give the aqueous solution desired. Therefore, the concentration of active compound is desirably selected in the range of 0.01 to 0.5 w/v % The amount of D-mannitol is, though somewhat varying with the amounts of other additives used together, usually in a range of 3 to 6 w/v %. The amount of glycine is usually in a range of 0.3 to 1.5 w/v %. In the present ophthalmic composition, other known additives, e.g. preservatives, bactericides and perfuming agents, may optionally be added in appropriate amounts.

The aqueous ophthalmic solution of the present invention may be formulated as follows. Thus, an acid addition salt of compound (I) (active compound) is first added to a part of distilled water, and is dissolved, under stirring and optionally is heated up to 50° C., therein. Next, D-mannitol, glycine and other additives as preservatives, bactericides and the like are added and dissolved into said solution. After adjusting the pH with hydrochloric acid, the remainder of distilled water is added and the thus obtained solution is filtered under sterile conditions and is filled into an appropriate ophthalmic container.

The invention shall be more fully explained in the following examples.

EXAMPLE 1

In the local administration tests, compound (I) was applied to one eye of healthy grown-up dog (male or female; body weight 10 to 14 kg; Beagle dog) being normal in sense of sight and other sensitive faculties and having no morphological abnormality in the eyes, and evaluated for the effect thereof.

The test ophthalmic composition was prepared according to the recipe of Example 4, so as to include 0.5 w/v % of compound (I) HCl salt.

One drop (about 0.04 ml) of the ophthalmic composition was applied to a conjunctival sac of one eye and a drop of physiologic saline was into the conjunctival sac of the other eye. Thus applied eyes were kept closed for 5 to 10 seconds to ensure the osmosis of the medicament administered. Intra-ocular pressure in the respective eye was measured by using an Alcon Pneumatonography, just before the treatment with said medicine, and 1 to 24 hours after said administration. At each time, one drop of 0.4% oxydibucaine HCl ophthalmic composition (Trade Mark: Benoxyl® 0.4%; Santen Seiyaku K.K.) was applied to and intra-ocular pressure was measured after 20 to 30 seconds thereafter.

The test results are shown in the following Table 1.

TABLE 1

| | Intra-ocular pressure measurement (mean ± standard error, mm Hg) | |
|---|---|---|
| | medicament administered | |
| measuring time | physiologic saline | compound (I) HCl |
| before administration | 21.0 ± 1.1 | 20.8 ± 0.9 |
| 1 hour later | 20.6 ± 0.5 | 20.0 ± 0.9 |
| 3 hours later | 21.4 ± 0.4 | 16.6 ± 1.0 |
| 5 hours later | 21.4 ± 0.2 | 15.4 ± 0.9 |
| 7 hours later | 19.8 ± 0.6 | 16.0 ± 1.3 |
| 9 hours later | 20.4 ± 0.7 | 17.6 ± 1.2 |
| 12 hours later | 21.2 ± 1.2 | 20.4 ± 0.7 |
| 24 hours later | 20.4 ± 0.7 | 20.6 ± 0.8 |

EXAMPLE 2

Using the same procedure as stated in Example 1, compound (I) was evaluated with 12 albino rabbits (male; body weight 2 to 3 kg, native kind). As the test medicaments, aqueous 0.5 w/v % and 0.25 w/v % compound (I) HCl solutions prepared according to Example 4 were used, as well as physiologic saline control solution.

Test results are shown in Table 2.

TABLE 2

| | Intra-ocular pressure measurement (mean ± standard error, mm Hg) | |
|---|---|---|
| measuring time | physiologic saline | compound (I) HCl |
| | | (0.5 w/v %) |
| before administration | 22.5 ± 0.6 | 22.5 ± 0.6 |
| 0.5 hour later | 22.7 ± 0.7 | 21.1 ± 0.8 |
| 1 hour later | 21.5 ± 1.0 | 18.9 ± 0.9 |
| 2 hours later | 21.4 ± 1.0 | 18.5 ± 0.9 |
| 3 hours later | 20.6 ± 0.8 | 18.2 ± 0.8 |
| 5 hours later | 23.3 ± 0.9 | 21.6 ± 0.8 |
| 7 hours later | 24.0 ± 0.7 | 22.8 ± 0.8 |
| 9 hours later | 22.4 ± 0.8 | 22.2 ± 0.8 |
| 24 hours later | 22.4 ± 0.8 | 22.5 ± 0.8 |
| | | (0.25 w/v %) |
| before administration | 21.8 ± 0.5 | 21.8 ± 0.5 |
| 0.5 hour later | 22.1 ± 0.5 | 20.7 ± 0.7 |
| 1 hour later | 22.4 ± 0.5 | 20.2 ± 0.6 |
| 2 hours later | 21.4 ± 0.6 | 19.8 ± 0.5 |
| 3 hours later | 21.3 ± 0.7 | 20.1 ± 0.6 |
| 5 hours later | 22.6 ± 0.6 | 22.1 ± 0.6 |
| 7 hours later | 22.9 ± 0.9 | 22.9 ± 0.8 |
| 9 hours later | 21.0 ± 0.7 | 21.0 ± 0.7 |
| 24 hours later | 22.0 ± 0.6 | 22.2 ± 0.6 |

EXAMPLE 3

In this example, irritant action of the present opthalmic composition was examined.

| Test ophthalmic composition A (present invention) (pH 5.5) | |
|---|---|
| compound (I) hydrochloride | 0.5 w/v % |
| D-mannitol | 5 |
| glycine | 0.5 |
| Benzalkonium chloride | 0.005 |
| hydrochloric acid | appropriate amount |
| distilled water | appropriate amount |
| Test ophthalmic composition B (control) (pH 5.6) | |
| compound (I) hydrochloride | 0.5 w/v % |

-continued

| | |
|---|---|
| D-mannitol | 5 |
| citric acid | 0.088 |
| sodium phosphate dibasic 2H₂O | 0.207 |
| Benzalkonium chloride | 0.005 w/v % |
| distilled water | appropriate amount |

Using a group of 5 rabbits (body weight 2.0 to 3.5 kg), one drop of test composition A was applied to left eye and one drop of test composition B was to right eye of each rabbit, and the responsive action was observed.

Test results are shown in Table 3.

TABLE 3

| | Irritant action test | |
|---|---|---|
| | responsive action | |
| rabbit No. | composition A | composition B |
| 1 | − | + |
| 2 | − | + |
| 3 | − | + + |
| 4 | − | + |
| 5 | − | + |

− ... no response, blinking 1-2 times
+ ... closing eye for more than 1 second after administration
+ + ... rubbing the eye with foreleg These test results show that the present ophthalmic composition A does not give any irritant action to the test animals.

EXAMPLE 4

The following composition was prepared.

| Component | % (w/v) |
|---|---|
| compound (I) hydrochloride | 0.5 |
| D-mannitol | 5 |
| glycine | 0.5 |
| Benzalkonium chloride | 0.005 |
| hydrochloric acid | appropriate amount |
| distilled water | to make 100 ml |

To a part of distilled water required, was added 500 mg of compound (I) hydrochloride and the mixture was stirred at room temperature to dissolve the active ingredient. Next, D-mannitol 5 g, glycine 500 mg and Benzalkonium chloride 5 mg were added in this order and dissolved in the same way. After adjusting pH of the solution to 5.5 with hydrochloric acid, the mixture was added with distilled water to make the total volume to 100 ml. The solution was filtered under sterile conditions. Thus prepared ophthalmic solution was very stable and no precipitation was observed after keeping at 40° C. for 3 months.

EXAMPLE 5

The following ophthalmic composition was prepared in the same way as stated in Example 4, using 100 mg of compound (I) acetate in place of 500 mg of compound (I) hydrochloride.

| Component | % (w/v) |
|---|---|
| compound (I) acetate | 0.1 |
| D-mannitol | 5 |
| glycine | 0.5 |
| Benzalkonium chloride | 0.005 |
| hydrochloric acid | appropriate amount |
| distilled water | to make 100 ml |

Thus obtained solution was very stable and no precipitation was observed even after keeping at 40° C. for 3 months.

| Component | % (w/v) |
|---|---|
| compound (I) maleate | 0.25 |
| D-mannitol | 4 |
| glycine | 1 |
| Benzalkonium chloride | 0.005 |
| hydrochloric acid | appropriate amount |
| distilled water | to make 100 ml |

To a part of the required distilled water, was added 250 mg of compound (I) maleate, and the mixture was heated to 30° C. and stirred to dissolve the active ingredient. To this solution, 4 g of D-manitol, 1 g of glycine and 5 mg of Benzalkonium chloride were added and dissolved in this order. After adjusting pH of the solution to 6.0 with hydrochloric acid, the solution was added with distilled water to make the volume to 100 ml, and thus obtained solution was filtered under sterile conditions. The ophthalmic solution thus prepared was very stable and no precipitation was observed even after being kept at 40° C. for 3 months.

What we claim is:

1. The method of treating glaucoma or ocular hypertension by topically applying to the eye an effective amount of 2-(3-tert.-butylamino-2-hydroxypropylthio)-4-(5-carbamoyl-2-thienyl)-thiazole or its acid addition salt to lower the intra-ocular pressure of the diseased eye.

2. The method of claim 1 wherein an inorganic or organic acid salt is used as an acid addition salt.

3. The method of claim 2 wherein the inorganic acid salt is borate, hydrochloride, sulfate, nitrate or phosphate.

4. The method of claim 2, wherein the organic acid salt is acetate, oxalate, lactate, maleate, succinate, tartarate, fumarate, citrate, glutarate, L-glutamate, d-camphorsulfonate or gluconate.

5. The method of claim 1, wherein a hydrochloride is used as the acid addition salt.

6. The method of claim 1, wherein an acetate is used as the acid addition salt.

7. The method of claim 1, wherein a maleate is used as the acid addition salt.

8. The ophthalmic composition for the treatment of glaucoma comprising an aqueous solution of an effective amount of acid addition salt of 2-(3-tert.-butylamino-2-hydroxypropylthio)-4-(5-carbamoyl-2-thienyl)-thiazole to lower the intra-ocular pressure of the eye and an isotonic agent.

9. The composition of claim 8, wherein an inorganic or organic acid salt is used as the acid addition salt.

10. The composition of claim 9, wherein the inorganic acid salt is borate, hydrochloride, sulfate, nitrate or phosphate.

11. The composition of claim 9, wherein the organic acid salt is acetate, oxalate, lactate, maleate, succinate, tartarate, fumarate, citrate, glutarate, L-glutamate, d-camphorsulfonate or gluconate.

12. The composition of claim 8, wherein a hydrochloride is used as the acid addition salt.

13. The composition of claim 8, wherein an acetate is used as the acid addition salt.

14. The composition of claim 8, wherein a maleate is used as the acid addition salt.

15. The ophthalmic composition of claim 8, wherein the composition contains D-mannitol as an isotonic agent.

16. The ophthalmic composition of claim 8, wherein the composition contains a combination of glycine and hydrochloric acid as buffer.

17. The ophthalmic composition according to claim 15, wherein the composition contains a combination of glycine and hydrochloric acid as buffer.

* * * * *